(12) United States Patent
Qu

(10) Patent No.: US 6,343,228 B1
(45) Date of Patent: Jan. 29, 2002

(54) METHOD AND APPARATUS FOR FLUORESCENCE IMAGING OF TISSUE

(75) Inventor: Jianan Qu, Kowloon (HK)

(73) Assignee: The Hong Kong University of Science and Technology (HK)

( * ) Notice: Subject to any disclaimer, the term of this patent is extended or adjusted under 35 U.S.C. 154(b) by 0 days.

(21) Appl. No.: 09/420,807

(22) Filed: Oct. 19, 1999

(51) Int. Cl.[7] .................................................. A61B 6/00
(52) U.S. Cl. ........................... 600/476; 600/478; 606/1; 606/2; 606/17; 606/18; 607/1; 607/88; 607/89; 359/483; 359/485; 359/489; 356/5.14; 356/323; 356/324; 356/327; 356/364
(58) Field of Search ................................ 600/310, 317, 600/339, 340, 341, 473, 342, 476, 478; 606/1, 2, 10, 11, 13, 14, 17, 18; 607/1, 88, 89; 356/4.01, 5.14, 322, 323, 324, 326, 327, 364, 366, 367; 359/483, 484, 485, 489

(56) References Cited

U.S. PATENT DOCUMENTS 6,104,939 A * 8/2000 Groner et al. ............... 600/322
6,104,945 A * 8/2000 Modell et al. ............... 600/473

* cited by examiner

Primary Examiner—Marvin M. Lateef
Assistant Examiner—Jeoyuh Lin
(74) Attorney, Agent, or Firm—Burns, Doane, Swecker & Mathis, L.L.P.

(57) ABSTRACT

Fluorescence imaging of tissue is used as a diagnostic tool in which geometric effects and specular reflections are compensated for by normalizing a fluorescence image with a cross-polarized image.

17 Claims, 11 Drawing Sheets

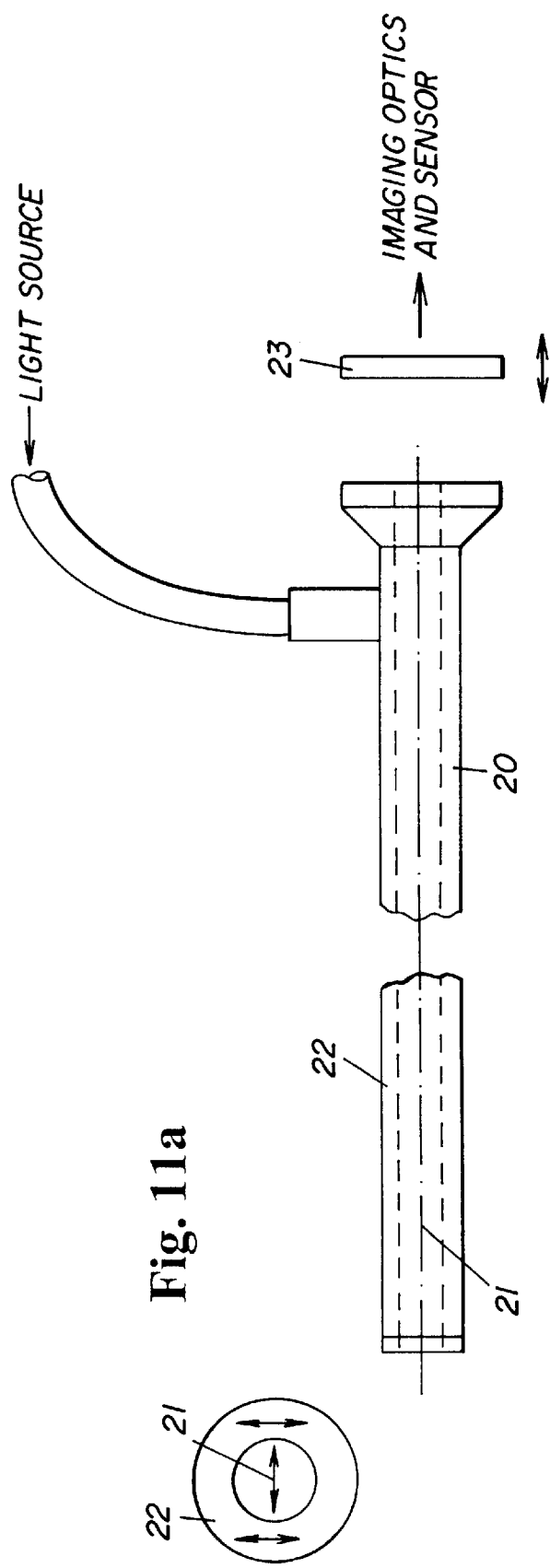

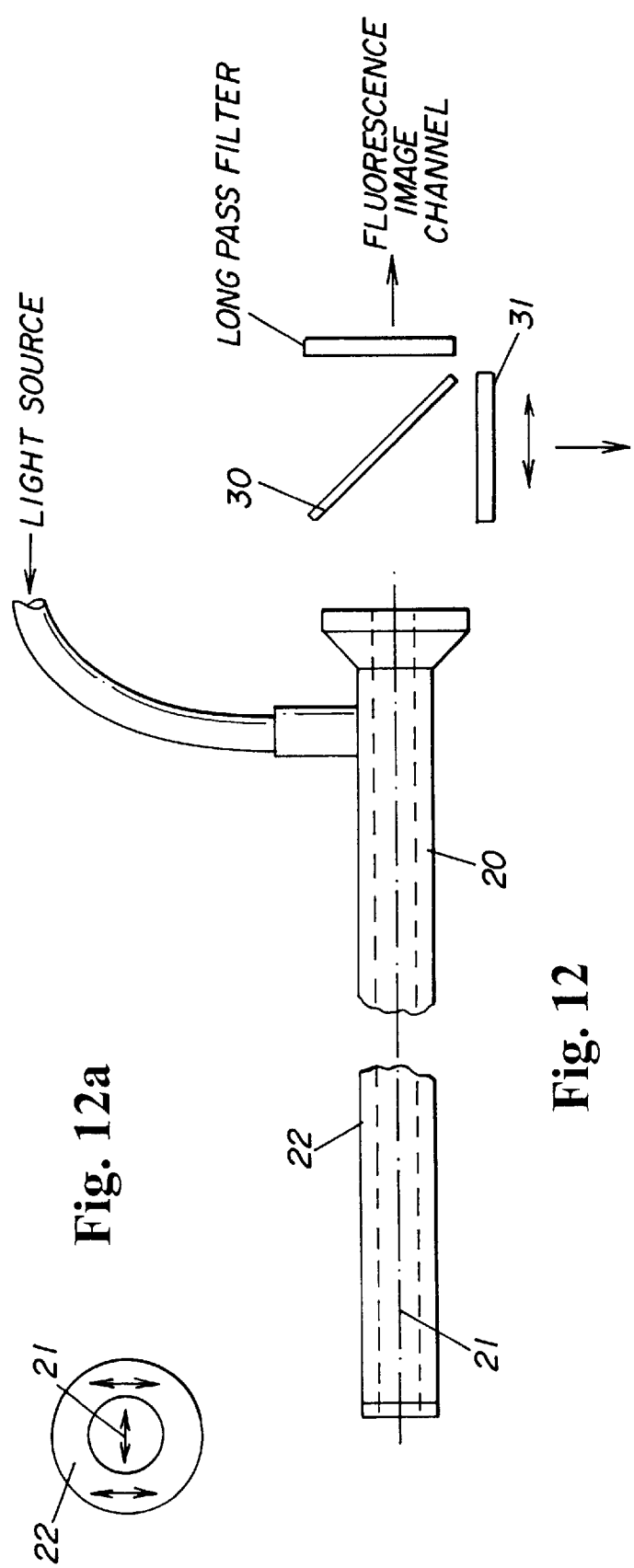

METHOD AND APPARATUS FOR FLUORESCENCE IMAGING OF TISSUE

FIELD OF THE INVENTION

This invention relates to a method and apparatus for the imaging of tissue using fluorescence techniques, and in particular for the endoscopic imaging of tissue in the diagnosis of various diseases such as cancer,

BACKGROUND OF THE INVENTION

Light induced fluorescence (LIF) imaging techniques have been proposed as an effective and non-invasive method to diagnose diseased tissue, especially for example the early stages of cancer. Autofluorescence from tissue is emitted from endogenous fluorophores when they are excited by low power short wavelength light. Such tissue autofluorescence can be used to determine biochemical and bio-morphological changes in the tissue. In particular studies have shown that the fluorescence yields of lesions in their early stages are normally lower than for surrounding healthy tissue. As a consequence LIF techniques have considerable potential for use as diagnostic tools.

The practical application of LIF techniques as effective diagnostic tools has, however, proved harder to achieve. One commonly used technique for in vivo study of tissue fluorescence uses a multiple optical fiber sensor to deliver the excitation light and to collect the fluorescence signal. The distal tip of the sensor is gently touched to the tissue surface to ensure that the fluorescence excitation and collection geometry is the same at different sites. The sensor is then moved from site to site to take the necessary readings. This point-by-point diagnosis has been successfully used for the detection of early cancers at many organ sites based on the contrast in fluorescence yield between healthy tissue and lesions. However, it is also time consuming and not practical for the examination of large tissue areas in clinical practice.

An imaging technique that enabled a relatively large tissue area to be imaged would be desirable. However, in the examination of a large area by an imaging device, the recorded fluorescence power will be strongly affected by the geometry of the excitation and collection system. For example, the separation of the source-sample-detector, the incident/emission angles and any irregularities in the sample surface will all have a large effect on the measurements making it very difficult to identify the fluorescence variations caused by biological changes in the tissue itself. These difficulties are particularly severe when internal tissues are being imaged in in vivo techniques using, for example, an endoscopic system.

A number of attempts have been made to overcome this geometrical difficulty. In one non-imaging approach the fluorescence signals were normalized to reflection signals taken from exactly the same sites. The results of this technique show that geometrical effects can be corrected, but that artifacts caused by the specular reflection of the tissue surface cause many false positives.

Another approach is to create a mathematical model of the geometrical effects which can then be used to correct the measured readings. However, the fluorescence power is a function of the emission angel and with a large image area of an irregular surface the emission angle will vary over a wide range and this cannot be compensated for mathematically without knowing the precise nature of the tissue surface, which is clearly completely impractical.

Another possibility is a digital image processing method in which the raw fluorescence image is normalized to a reference image which is the raw image processed by a moving average algorithm. This method can correct for geometrical errors providing that the moving average algorithm is carefully chosen. However, the validity of this method is dependent on the ratio of the size of the lesion over the imaged area and the degree of non-uniformity of the fluorescence excitation and collection geometry. To ensure the filtering out of lesions and the keeping of the excitation and collection nonuniformities in the reference image area, the algorithm requires that the lesion width is much smaller than the imaged area. The variation of fluorescence caused by geometrical effects must also be assumed to be a slowly varying function over the tissue surface because the algorithm cannot distinguish a lesion from geometrical artifacts of which the spatial frequency distribute in the same region as the lesion.

SUMMARY OF THE INVENTION

According to the present invention there is provided apparatus for imaging the autofluorescence yield of a sample, comprising: (a) means for illuminating and exciting an area of said sample to stimulate autofluorescence, (b) means for forming a fluorescence image of the illuminated area, (c) means for forming a cross-polarized reflection image of the area, and (d) means for producing an output image by normalizing the fluorescence image to said cross-polarized image.

Preferably the output producing means forms a ratio image of the fluorescence image and the cross-polarized image.

In a preferred embodiment the apparatus comprises means for detecting the fluorescence image and the cross-polarized image and means for digitally processing the detected images. For processing the images the apparatus may comprise computer means provided with a frame grabber. Preferably the computer means may take an average of multiply detected images.

The apparatus is preferably incorporated as an endoscope and preferably comprises two optical channels, a first channel for providing light for illuminating and stimulating an area of tissue, and a second channel for collecting fluorescence and reflected light. The apparatus may include means for linearly polarizing the illuminating and stimulating light, and may further comprise imaging optics for forming fluorescence and reflection images from light collected by the second channel. The apparatus most preferably includes a cross-polarizer linearly polarized at an angle of 90° to the illumination to collect the cross-polarized reflection image.

In one embodiment the first optical channel may extend along the central optical axis of an endoscope and the second channel may be annular in cross-section and may surround the first channel. Alternatively the first and second channel may be formed adjacent one another extending parallel to the central axis of an endoscope.

Viewed from another broad aspect the present invention provides a method for imaging the autofluorescence yield of a sample, comprising: (a) illuminating and exciting an area of said sample to stimulate autofluorescence, (b) forming a fluorescence image of said illuminated area, (c) forming a cross-polarized reflection image of the said area, and (d) producing an output image by normalizing the fluorescence image by the cross-polarized image.

Preferably the normalizing step comprises forming a ratio image of the fluorescence image and the cross-polarized image. In an embodiment of the invention digital images may be formed and are digitally processed. The images may be processed by a computer provided with a frame grabber. Preferably multiple images of the same area are obtained and are averaged.

BRIEF DESCRIPTION OF THE DRAWINGS

Some embodiments of the invention will now be described by way of example and with reference to the accompanying drawings, in which:

FIG. 11 shows an apparatus according to a second embodiment of the invention, FIG. 12 shows a modification of the apparatus of FIG. 11.

DETAILED DESCRIPTION OF PREFERRED EMBODIMENTS

Figure 1:
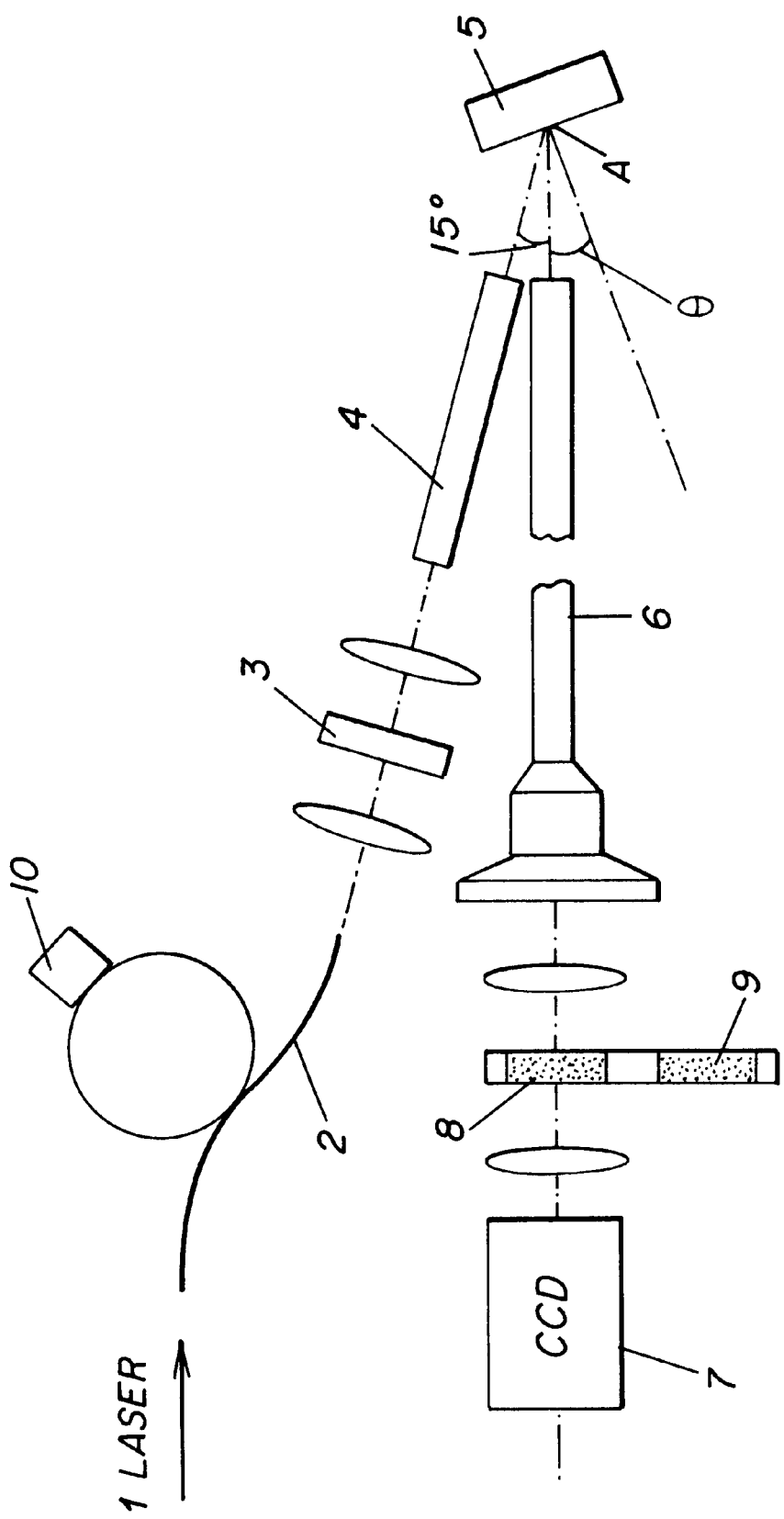
FIG. 1 is a schematic view of apparatus according to a first embodiment of the present invention.

Before discussing certain practical embodiments of the present invention, the efficacy of the principles of the present invention will be described with reference to an experimental arrangement shown in FIG. 1. The experimental apparatus comprises an excitation source 1 in the form of a solid-state frequency doubled laser with 200 mW output power at a wavelength of 457 nm. The laser light is delivered to the sample surface through an illumination optics comprising a multimode optical fiber 2 of 20 $\mu$m in diameter, a linear polarizer 3 and microlenses 4 (1.6 mm in diameter). The fluorescence and reflection signals from a sample 5 are collected by a standard endoscope 6 and imaged to an 8-bit CCD camera 7. The angle between the optical axes of the illumination optics and of the endoscope is about 15°. The distal tips of the endoscope and of the illumination optics are physically attached to each other and are about 10 mm away from the surface of the sample. The imaged area on the sample surface is about 10 mm×10 mm and is smaller than the illuminated area. To vary the illumination and collection geometry in order to simulate clinical use, the sample may be rotated about an axis perpendicular to the surface of the sample and passing through the intersection of the illumination and collection optical axes. Light collected from the sample is passed through either a long pass filter 8 or a cross-polarizer 9 that is at 90° to the polarizer 3 in the illumination optics. Cross-polarizer 9 and long pass filter 8 may be interchanged in the collection optics to select either a cross-polarized image or a fluorescence image respectively, the images being grabbed by a frame grabber at a rate of 25 frames per second. To improve the signal to noise ratio, the fluorescence image is formed from an average of 16 frames. As will be explained in more detail below, to compensate for geometrical and illumination irregularities, the fluorescence image is normalised by reference to the cross-polarized image in a computer.

The signal to noise ratio of the normalised image is dependent on the quality of the fluorescence and cross-polarized images. To improve the quality of the image by reducing the effects of the "speckle effect" on the quality of the images, apart of the illumination optics may be driven by a voice coil 10 to introduce a modulation that has the effect of changing the speckle pattern into a time-varying function that can be averaged out if the modulation frequency is set at about 600 Hz.

To experimentally demonstrate the efficacy of the present invention, tissue-simulating samples may be constructed made of gelatin with 20% solids dissolved in boiling deionized water, polystyrene spheres of 0.55 $\mu$m in diameter, fluorescent dye mixture and dominantly absorbing blood. The samples are made in accordance with well documented procedures.

Figure 2:
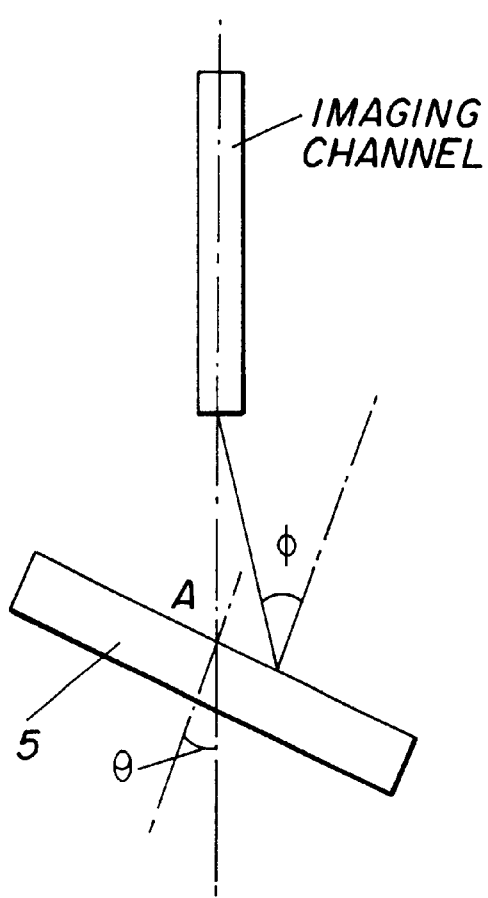
FIG. 2 shows the form of a first sample used for demonstrating the present invention.

To demonstrate that the present invention is capable of correcting for geometrical effects, six samples are made in accordance with table 1 below. All the samples are homogenous and have a flat surface as shown in FIG. 2.

TABLE 1

| Sample No. | Blood content (v/v %) | Polystyrene conc. (w/w %) |
|---|---|---|
| 1 | 2.5 | 0.25 |
| 2 | 5.0 | 0.25 |
| 3 | 7.5 | 0.25 |
| 4 | 2.5 | 0.5 |
| 5 | 5.0 | 0.5 |
| 6 | 7.5 | 0.5 |

The imaging geometry was changed by rotating the sample and by changing the illumination angle $\theta$ between 0° and 60° in increments of 15°. For a fair comparison, the mean gray levels of the raw fluorescence images and the normalised images were adjusted to 128, ie half the full gray level of an 8-bit image.

Figure 3A:
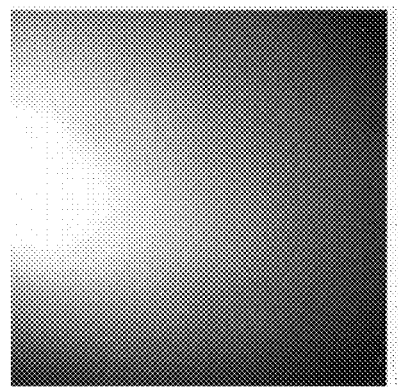
FIG. 3 shows the raw fluorescence data obtained using the apparatus of FIG. 1 with the sample of FIG. 2.
Figure 4A:
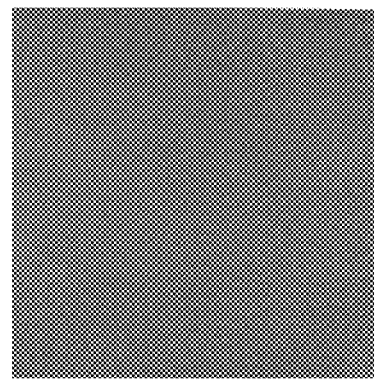
FIG. 4 shows the normalised data obtained using the apparatus of FIG. 1 with the sample of FIG. 2.
Figure 3B:
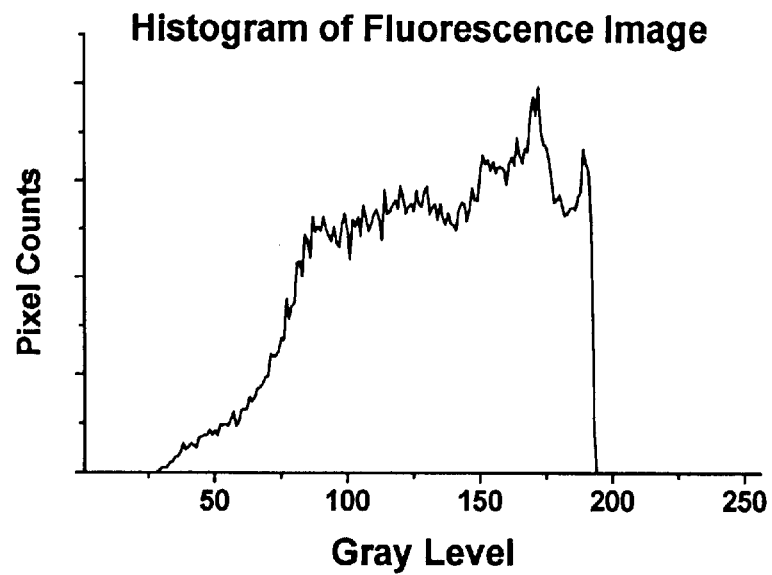
Figure 4B:
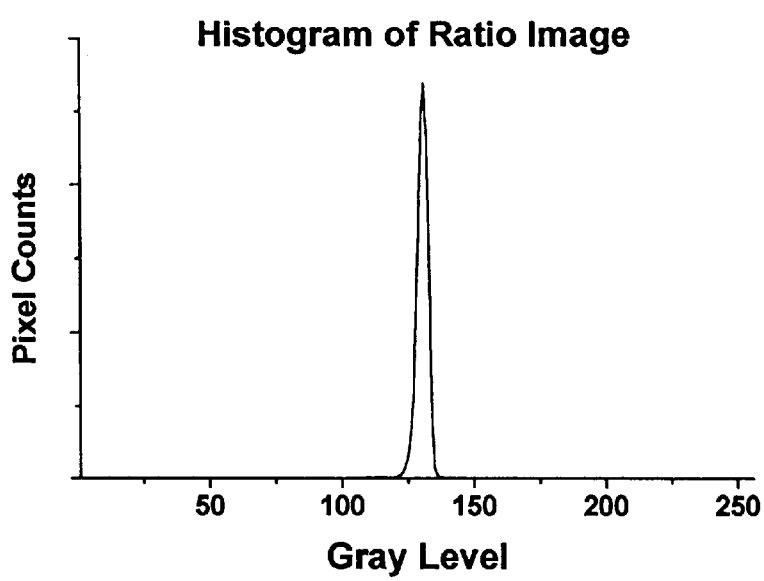

FIG. 3 shows a raw fluorescence image and a corresponding grey level histogram. As can be seen from both the raw image and the histogram, the image is highly non-uniform and the gray levels vary widely in range, in spite of the fact that the sample is homogenous and the surface of the sample is flat. FIG. 4 shows the corresponding image and grey level histogram when the raw fluorescence image has been normalized by taking the ratio of the raw fluorescence image with the cross-polarized image. It will be seen that the image is uniform and there grey level has a very narrow distribution around 128. Over the varying illumination angles, the standard deviations of the gray levels in the raw fluorescence images vary from 24 to 41, while the standard deviations of the ratio images vary from 1.8 to 4.5.

Figure 5:
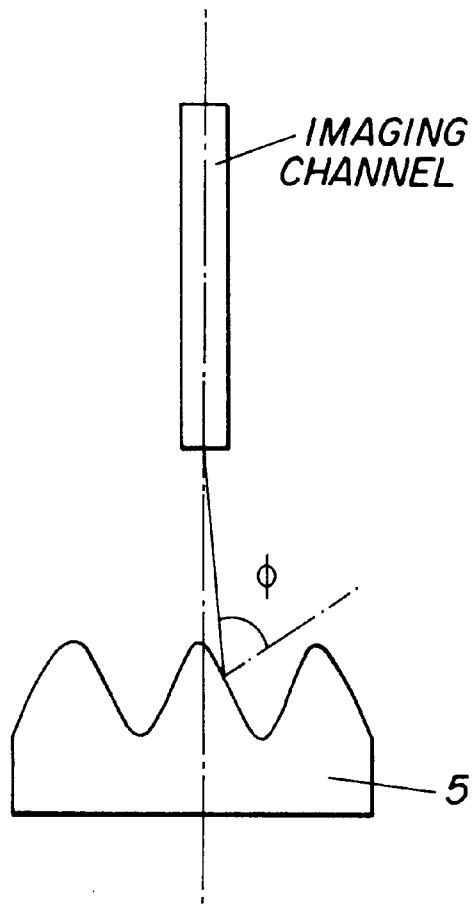
FIG. 5 shows a second sample used for demonstrating the present invention.
Figure 6A:
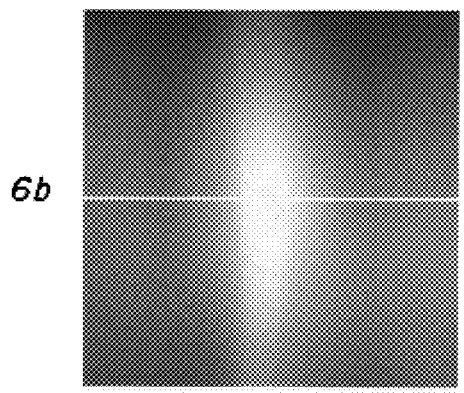
FIG. 6 shows the raw fluorescence data obtained using the apparatus of FIG. 1 with the sample of FIG. 5.
Figure 7A:
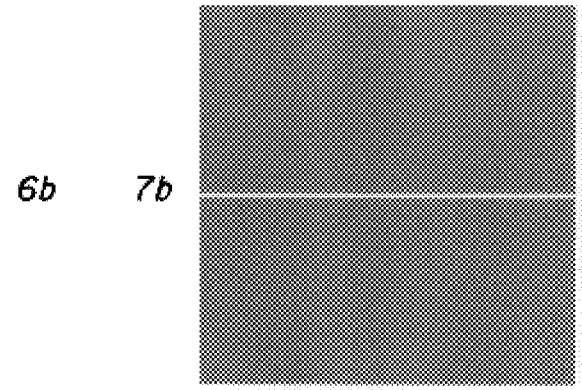
FIG. 7 shows the normalised data obtained using the apparatus of FIG. 1 with the sample of FIG. 5.
Figure 6B:
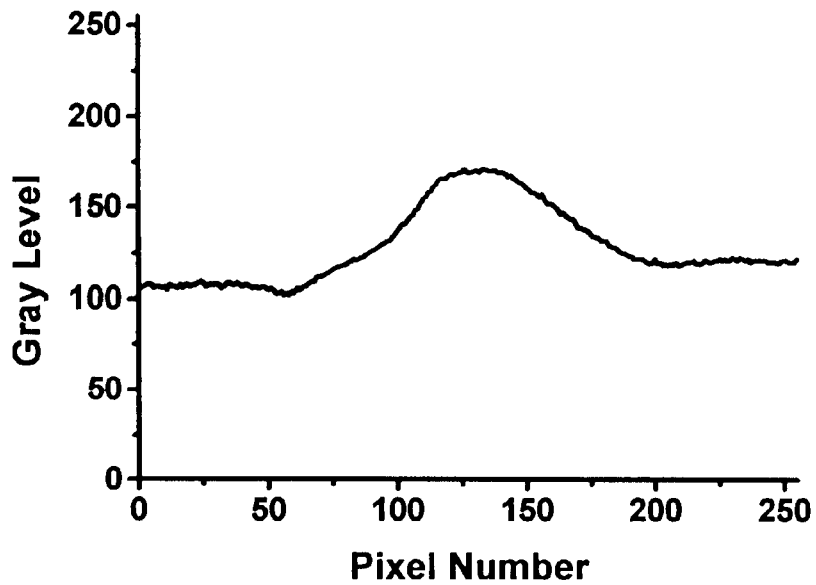
Figure 7B:
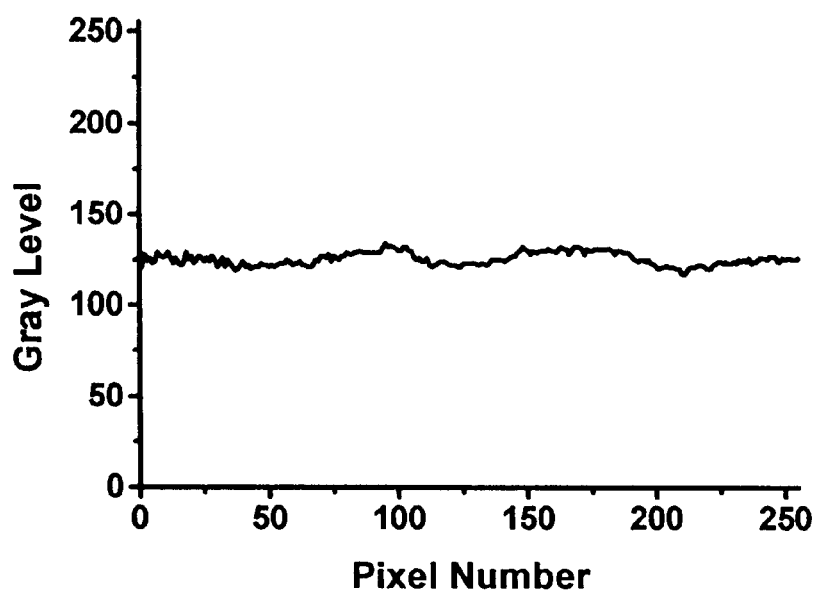

The samples in Table 1 are all homogenous and have a flat surface. Inhomogenity in the raw fluorescence images therefore results from geometrical factors in the imaging and collection optics and the results shown in FIGS. 3 and 4 show that the present invention is able to effectively compensate for such geometrical factors. FIG. 5 shows an homogenous sample (blood content 5% v/v polystyrene content 0.35% w/w) made with an irregular surface. Fluorescence and cross-polarized images are taken at $\theta=0°$ and the raw fluorescence and ratio images and gray level line profiles are shown in FIGS. 6 and 7 respectively. It can be seen that the inhomogenity in the raw fluorescence image (FIG. 6) is corrected in the normalised ratio image (FIG. 7).

Figure 8A:
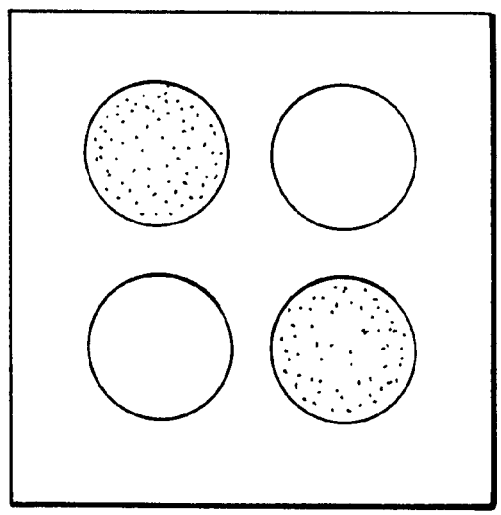
FIG. 8 shows a further sample used for demonstrating the present invention.
Figure 8B:
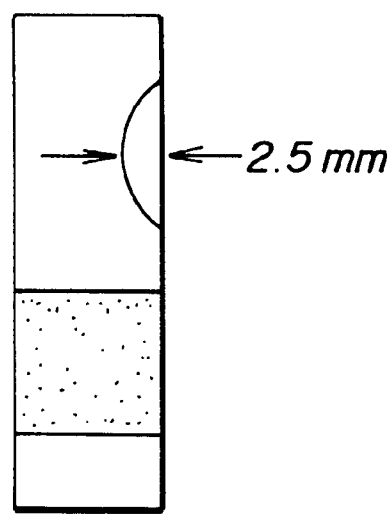

To demonstrate that the present invention can detect small variations in fluorescence yield, such as might be caused to tissue by the early stages of diseases such as cancer, inhomogeneous tissue simulating samples were prepared. FIG. 8 shows a first form of tissue simulating sample used in this manner. In this Figure, the shaded areas represent areas of the sample where the sample forming mixture has been replaced by a mixture of slightly lower concentration of fluorescent dyes to simulate lesions. The areas are set to give a fluorescence yield of approximately 80% of the remainder of the tissue simulating sample. The blood concentration and microsphere concentration were set at 5% and 0.35% respectively. Two holes of smooth walls were also constructed to function as artifacts to determine the ability of the present invention to distinguish between areas of lower fluorescence yield and artifacts.

Figure 9:
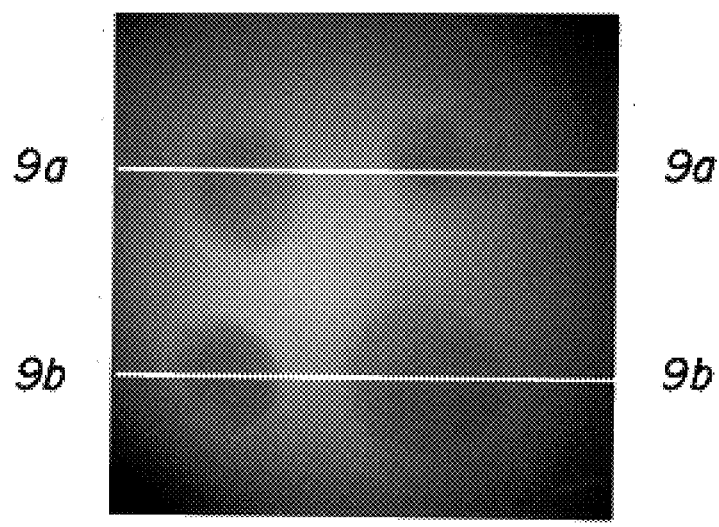
FIG. 9 shows the raw fluorescence data obtained using the apparatus of FIG. 1 with the sample of FIG. 8.
Figure 10:
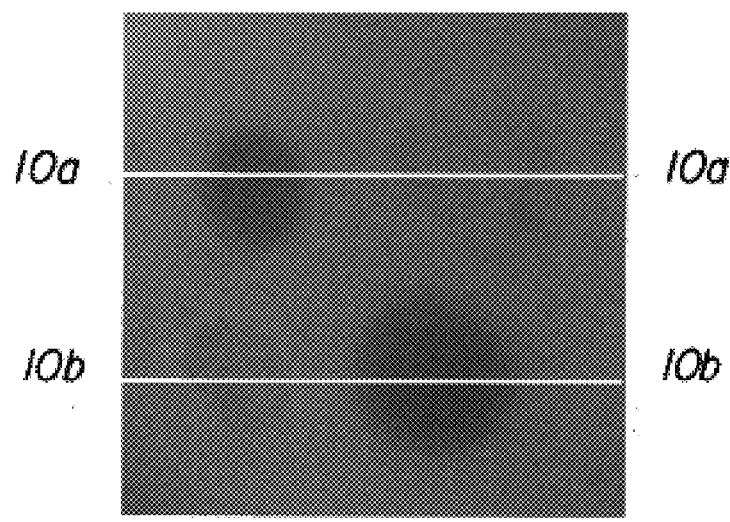
FIG. 10 shows the normalised data obtained using the apparatus of FIG. 1 with the sample of FIG. 8.
Figure 9A:
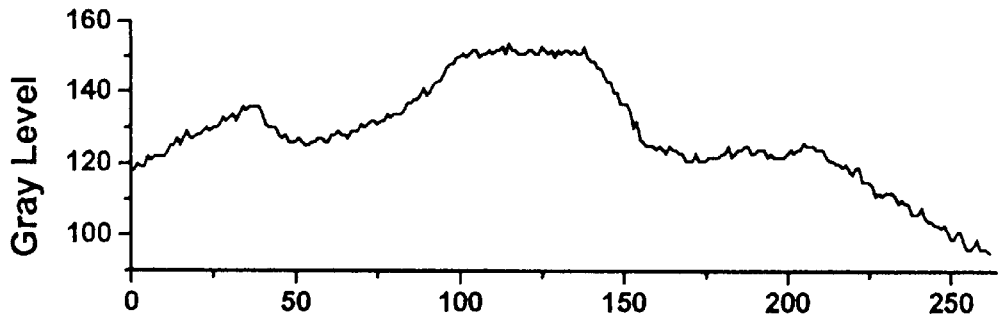
Figure 9B:
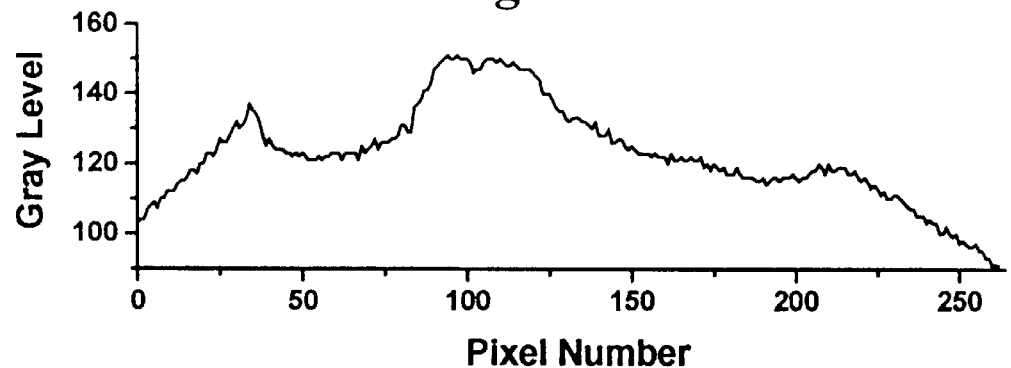
Figure 10A:
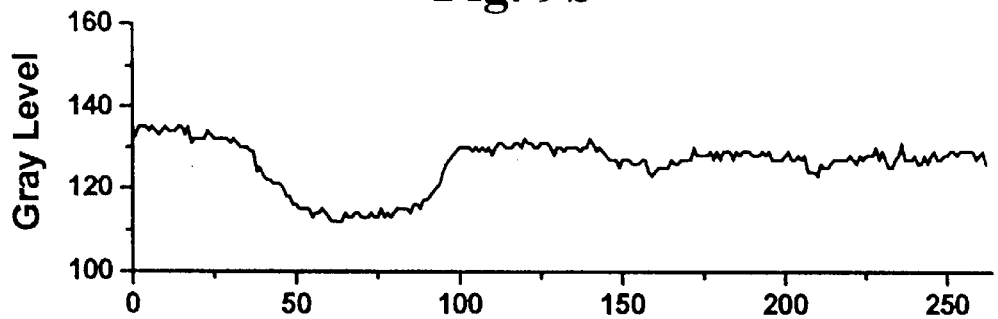
Figure 10B:
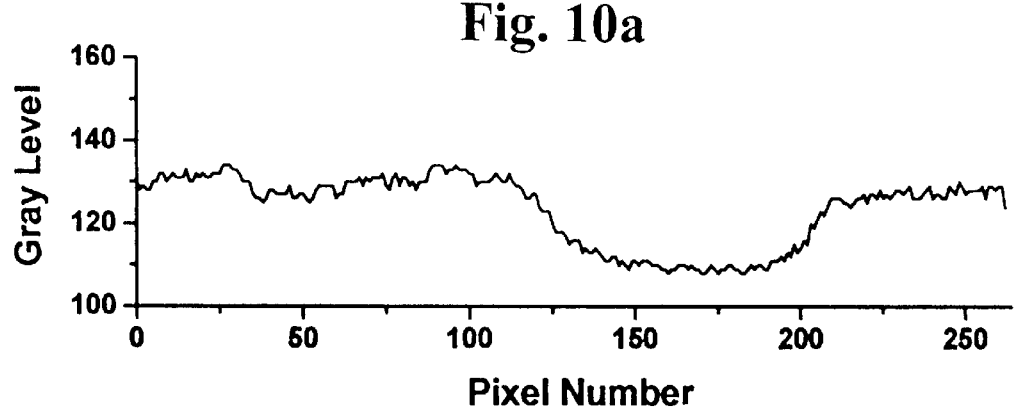

FIG. 9 shows the raw fluorescence image and the corresponding line profiles, while FIG. 10 shows the corresponding image normalised by the cross-polarized image together with the corresponding line profile. It will be noted that the raw image in FIG. 9 is incapable of differentiating between the two images of reduced fluorescence yield (top left and bottom right in the Figure) and the geometric artifacts created by the two holes (top right and bottom left). In contrast the normalised image shown in FIG. 10 shows only the areas where a reduced fluorescence yield has been created.

In the embodiment shown in FIG. 1 separate illumination and collection optical systems are provided closely adjacent each other. In a real-life clinical situation, however, it would be preferable for the illumination/excitation optics and the collection optics to be integrated into a single endoscopic apparatus. An example of such an apparatus is shown in FIG. 1. The apparatus comprises a rigid or flexible endoscope 20 comprising two optical channels 21,22. A first optical channel 21 is formed extending along the central axis of the endoscope and comprises the imaging channel for collecting the image of the tissue and returning the image to collection optics shown in the right of the picture and which will be described further below. Surrounding the imaging channel 21 is an annular illumination channel 22. The illumination channel 22 creates polarized light from a remote light source and is used to illuminate the tissue and for eliminating the specular reflection. The imaging optics may, as in the embodiment of FIG. 1, comprise a sensor such as a CCD camera and a computer provided with a frame grabber and means for digitally processing the imaged data. An external cross-polarizer or long pass filter 23 may be provided between the end of the endoscope 20 and the imaging optics. The cross-polarizer has a polarization at 90° to the polarization of the illumination light. The polarizer 23 may be moved into a position in which it is in the optical path between the endoscope 20 and the imaging optics so as to provide the cross-polarized image. The polarizer 23 may be removed from the path and replaced with a long pass filter so as to enable the raw fluorescence data to be recorded.

FIG. 12 shows an alternative embodiment in which instead of requiring the cross-polarizer to be moved into and out of the optical path, a beam splitter 30 in the form of a dichroic mirror is used to direct part of the beam to a cross-polarizer 31 to form the cross-polarized image.

Figure 13:
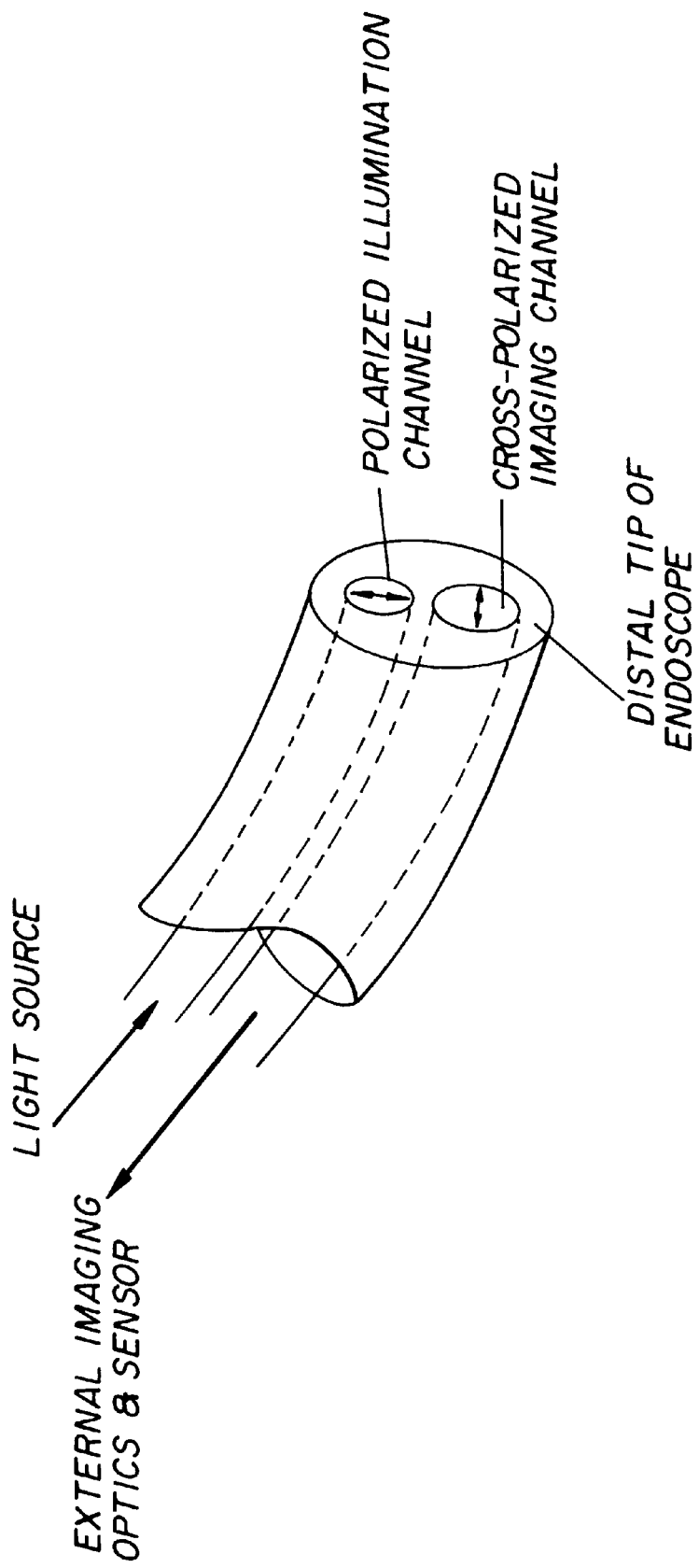
FIG. 13 shows a modification of the apparatus of FIG. 12.

FIG. 13 shows a modification of the distal tip of an endoscope which can be either rigid or flexible. Two polarizers with polarization directions perpendicular to each other are placed at the tip of the illumination channel and imaging channel. The external imaging optics for recording the cross-polarized image and the fluorescence is the same as shown in FIG. 12, the only difference being that the external cross-polarizer is removed.

What is claimed is:

1. Apparatus for imaging the autofluorescence yield of a sample, comprising:

(a) means for illuminating and exciting an area of said sample to stimulate autofluorescence, (b) means for forming a fluorescence image of the illuminated area, (c) means for forming a cross-polarized reflection image of the area, and (d) means for producing an output image by normalizing the fluorescence image to said cross-polarized image.

2. Apparatus as claimed in claim 1 wherein the output producing means forms a ratio image of the fluorescence image and the cross-polarized image.

3. Apparatus as claimed in claim 1 comprising means for detecting said fluorescence image and said cross-polarized reflection image and means for digitally processing said detected images.

4. Apparatus as claimed in claim 3 comprising computer means provided with a frame grabber.

5. Apparatus as claimed in claim 4 wherein said computer means is provided with means for taking an average of multiple detected images.

6. Apparatus as claimed in claim 1 comprising an endoscope.

7. Apparatus as claimed in claim 6 wherein said endoscope comprises two optical channels, a first channel for providing light for illuminating and stimulating said area of tissue, and a second channel for collecting fluorescence and reflected light.

8. Apparatus as claimed in claim 7 wherein a first said channel is formed extending along the central axis of said endoscope and the second said channel is annular in cross-section and surrounds said first channel.

9. Apparatus as claimed in claim 7 wherein said first an second channel are formed adjacent one another extending parallel to the central axis of said endoscope.

10. Apparatus as claimed in claim 6 including means for linearly polarizing said illuminating and stimulating light.

11. Apparatus as claimed in claim 10 comprising imaging optics for forming fluorescence and reflection images from light collected by said second channel.

12. Apparatus as claimed in claim 11 including a cross-polarizer linearly polarized at an angle of 90° to said illuminating light.

13. A method for imaging the autofluorescence yield of a sample, comprising:
   (a) illuminating and exciting an area of said sample to stimulate autofluorescence,
   (b) forming a fluorescence image of said illuminated area,
   (c) forming a cross-polarized reflection image of the said area, and
   (d) producing an output image by normalizing the fluorescence image by the cross-polarized image.

14. A method as claimed in claim 13 wherein said normalizing step comprises forming a ratio image of the fluorescence image and the cross-polarized image.

15. A method as claimed in claim 13 wherein digital images are formed and digitally processed.

16. A method as claimed in claim 15 wherein said images are processed by a computer provided with a frame grabber.

17. A method as claimed in claim 16 wherein multiple images of the same area are obtained and are averaged.

* * * * *